United States Patent
Thavonekham

[11] Patent Number: 5,925,762
[45] Date of Patent: Jul. 20, 1999

[54] PRACTICAL SYNTHESIS OF UREA DERIVATIVES

[75] Inventor: Bounkham Thavonekham, Longueuil, Canada

[73] Assignee: Boehringer Ingelheim (Canada) Ltd., Laval, Canada

[21] Appl. No.: 08/931,006

[22] Filed: Sep. 15, 1997

Related U.S. Application Data

[60] Provisional application No. 60/026,202, Sep. 17, 1996.

[51] Int. Cl.$^6$ .................. C07D 213/04; C07C 275/28
[52] U.S. Cl. .................. 546/280; 544/390; 544/391; 546/226; 548/190; 548/197; 548/198; 548/538; 558/417; 564/48; 564/52; 564/56
[58] Field of Search .................. 564/48, 52, 56; 548/190, 198, 197, 538; 546/226, 280; 544/390, 391; 558/417

[56] References Cited

U.S. PATENT DOCUMENTS 3,161,676  12/1964  Adams .................. 260/553
5,420,164   5/1995  Mishina et al. .................. 514/596

*Primary Examiner*—Shailendra Kumar
*Attorney, Agent, or Firm*—R. P. Raymond; M-E. M. Devlin; A. R. Stempel

[57] ABSTRACT

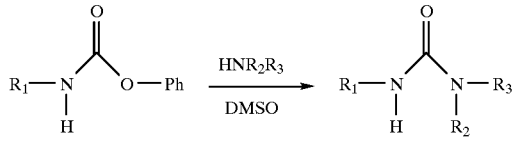

A very mild and efficient approach for the synthesis of ureas is described. Phenyl carbamates were used as intermediates for the preparation of N,N'- substituted ureas. The carbamates were treated with an approximate stoichiometric amount of amine in dimethyl sulfoxide at ambient temperature, generating the ureas in high yield. The reaction was simple, safe, fast, inexpensive, and amenable to large scale production of the product.

6 Claims, No Drawings

PRACTICAL SYNTHESIS OF UREA DERIVATIVES

This application is a continuation of provisional application No. 60/026,202, filed Sep. 17, 1996.

FIELD OF THE INVENTION

This invention relates to a process to prepare urea derivatives, including ureas and thioureas. More specifically, this invention relates to a process for the preparation of urea derivatives from amines and provides a facile route to a series of urea derivatives.

BACKGROUND OF THE INVENTION

Urea derivatives have found use in a wide variety of areas, including the pharmaceutical industry. More explicitly, Matsuda, Med. Res. Reviews, 1994, 14, 271, reports a number of urea compounds as acyl CoA:cholesterol O-acyl transferase (ACAT) inhibitors useful for the treatment of atherosclerosis.

In general, the preparation of urea derivatives from amines is based on the use of toxic phosgene, thiophosgene, phosgene substitutes or carbonic acid derivatives such as carbonyldiimidazole and derivatives. The most widely used method has involved the use of isocyanates or isothiocyanates. However, the preparation of isocyanates or isothiocyanates usually involves the use of phosgene or thiophosgene.

Recently improved methods for the synthesis of isocyanate derivatives have been reported. U.S. Pat. No. 4,294,774 (Henson et al.), and Japanese patent JP 63-150,255 (Takano et al.) report several processes involving the aminolysis of alkylcarbamates. Very often, these processes require drastic reaction conditions (high temperature) such as in U.S. Pat. No. 3,161,676 (Adams et al.).

Recently, novel methods for the preparation of urea derivatives were described involving the treatment of an alkylcarbamate with a magnesium amide (Basha, A., Tetrahedron. Lett., 1988, 29, 2525)., the DMAP-catalyzed reaction of an amine with a tert-butyl carbamate (Knölker, H.-J.; Braxmeier, T.; Schlechtingen, G.; Synlett, 1996, 502; Angew. Chem. Int. Ed. Engl., 1995, 34, 2497), the deprotonation of N-Boc with a strong base and reaction of the isocyanate thus formed with an amine (Lamothe, M.; Perez, M.; Colovray-Gotteland, V.; Halazy, S.; Synlett, 1996, 507), the reaction of an unsymmetrical diaryl carbonate (Freer, R.; McKillop, A., Synth. Commun., 1996, 26, 331) or an S,S-dimethyl dithiocarbonate with an amine (Leung, M.-K.; Lai, J.-L.; Lau, K.-H.; Yu, H.-H., Hsiao, H.-J., J. Org. Chem., 1996, 61, 4175). These methods call for harsh conditions, long reaction times and occasionally a large excess of amine.

SUMMARY OF THE INVENTION

In accordance with the present invention, there is provided an efficient and mild process for the synthesis of a urea derivative, including a urea or a thiourea, via the aminolysis of the respective phenyl carbamate or phenyl thiocarbamate under neutral and mild conditions using dimethyl sulfoxide as solvent. An added advantage of the process is that the phenyl carbamate group or phenyl thiocarbamate group can also be used as a protecting group for the amine functionality.

Therefore, there is provided a process for preparing a urea derivative which comprises:

reacting a primary phenyl carbamate or phenyl thiocarbamate with ammonia, a primary amine, or a secondary amine in dimethyl sulfoxide solution to give the corresponding urea derivative.

DETAILED DESCRIPTION OF THE INVENTION

The term "lower alkyl" as used herein, either alone or in combination with another radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "lower alkoxy" as used herein, either alone or in combination with another radical, means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "lower alkanoyl" as used herein means a straight chain 1-oxoalkyl containing from two to six carbon atoms or a branched chain 1-oxoalkyl containing from four to six carbon atoms; for example, acetyl, propionyl(1-oxopropyl) and 2-methyl-1-oxopropyl.

The symbol "Ph" represent a phenyl group. Other symbols used herein are: Me for methyl, Et for ethyl, Bu for butyl, tBu for tert-butyl (also known as 1,1-dimethylethyl), and Bn for phenylmethyl (also known as benzyl).

The term "thiocarbamate", "phenyl thiocarbamate" or "carbamic acid O-ester", as used herein, refers to a thiocarbamate having a partial structure wherein a sulfur atom is attached via a double bond to a carbon atom which in turn bears an ether oxygen (i.e. an oxy group). The thiocarbamate radical can be represented by the structure N—C(=S)—O—.

The term "urea derivative", as used herein includes both a urea or thiourea type compound, i.e. compounds having either the partial structure —N—C(=O)—N— or N—C(=S)—N—.

An embodiment of the process comprises reacting the carbamate derivative of the formula 1:

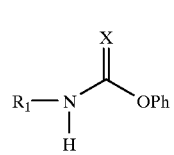

(1)

wherein X is oxo or thioxo and $R_1$ is lower alkyl, a monosubstituted or disubstituted lower alkyl wherein the substituent is selected from the group consisting of lower alkoxycarbonyl and phenyl; 4-{1-(phenylmethyl)piperidinyl}, phenyl or phenyl monosubstituted with a substituent selected from the group consisting of lower alkoxy, lower alkoxycarbonyl, cyano, lower alkanoyl and (lower alkoxycarbonyl)-(lower alkyl); 4-(2-amino-4-thiazoyl)phenyl or 4-{2-{{(1,1-dimethylethoxy)carbonyl}amino}-4-thiazolyl}phenyl with an amine of the formula Q:

$HNR_2R_3$ (Q)

wherein $R_2$ is hydrogen or lower alkyl and $R_3$ is hydrogen, lower alkyl, lower alkyl monosubstituted with phenyl or 2-pyridinyl; phenyl or 4-{1-(phenylmethyl)piperidinyl}; or $R_2$ and $R_3$ together with the nitrogen to which they are attached form a ring selected from the group consisting of

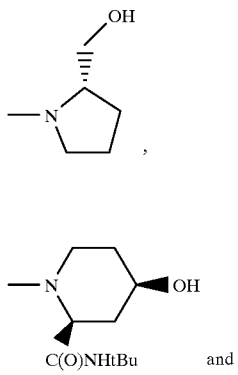

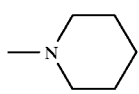

C(O)NHtBu    and

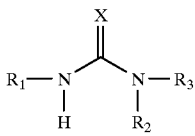

to obtain the corresponding urea derivative of formula 2:

$$\underset{\underset{H}{|}}{R_1}-N-\overset{X}{\overset{\|}{C}}-\underset{\underset{R_2}{|}}{N}-R_3 \qquad (2)$$

wherein X, $R_1$, $R_2$ and $R_3$ are as defined herein.

The process for the preparation of the urea derivatives is performed in a solution of dimethyl sulfoxide. The molar ratio of the phenyl carbamate or phenyl thiocarbamate to ammonia or to the primary or secondary amine generally ranges from 1:1 to 1:1.1, preferably 1:1.05, respectively. Excessive amounts of reactants are avoided. The duration of the reaction varies generally from that of an instantaneous reaction to about three hours dependent on the nature of the carbamate or thiocarbamate (e.g. aliphatic vs aromatic, see hereinafter) and on the nucleophilicity of the amine. The reaction temperature varies generally from about room temperature (ca 22° C.) to 100° C. Usually the reaction can be performed efficiently at room temperature.

In one aspect, the present invention provides a process wherein the urea derivative is N'-{4-{2-{{(1,1-dimethylethoxy)carbonyl}amino}-4-thiazolyl}phenyl}-N-methyl-N-{2-(2-pyridinyl) ethyl}urea, the primary phenylcarbamate is phenyl N-{4-{2-{{(1,1-dimethylethoxy) carbonyl}amino}-4-thiazolyl}phenyl}carbamate and the amine is N-methyl-N-{2-(2-pyridinyl)ethyl}amine. The antiviral property of this urea derivative is noted in example 5, hereinafter.

In another aspect, the present invention provides a process wherein the urea derivative is N'-{4-(2-amino-4-thiazolyl) phenyl}-N,N-dibutylurea, the primary phenylcarbamate is phenyl N-{4-(2-amino-4-thiazolyl)phenyl}carbamate and the secondary amine is N,N-dibutylamine. The antiviral property of this urea derivative is noted in example 5 hereinafter.

As noted hereinbefore, urea compounds have also be used as ACAT inhibitors. Such compounds can be prepared by the present process. For example, N-2,6-di(1-methylethyl) phenyl-N'-2,2-diphenylethyl urea can be prepared by the process disclosed herein; namely by the condensation of phenyl 2,6-di(1-methylethyl)phenylcarbamate with (2,2-diphenylethyl)amine in dimethyl sulfoxide.

Phenyl carbamates and phenyl thiocarbonates were obtained via standard methods. They were stable, often crystalline and exhibited a strong UV chromophore. After reaction with an amine (usually 1.05 molar equivalents) in dimethyl sulfoxide at ambient temperature, they generated the urea derivatives in high yield. No other base was required for this substitution. Several representative examples are shown in Table 1.

TABLE 1

Preparation of Ureas from Phenyl Carbamates and melting point.

| | carbamates 1 | amine[a] | time[b] | ureas 2 | yield[c] | mp (°C.) |
|---|---|---|---|---|---|---|
| a | MeO(O)C-C₆H₄-NH-C(O)-OPh | (S)-prolinol (2-hydroxymethylpyrrolidine) | 15 min | MeO(O)C-C₆H₄-NH-C(O)-N(pyrrolidine-CH₂OH) | 87%[f] | 140–142 |
| b | MeO(O)C-C₆H₄-NH-C(O)-OPh | HCl·HNMe₂[d] | 30 min | MeO(O)C-C₆H₄-NH-C(O)-NMe₂ | 80% | 168–170 |
| c | NC-C₆H₄-NH-C(O)-OPh | PhNH₂ | 85° C., 1 h | NC-C₆H₄-NH-C(O)-NHPh | 87.5% | 208–210 |
| d | MeC(O)-C₆H₄-NH-C(O)-OPh | 4-hydroxy-2-(C(O)NHtBu)piperidine | 1 h 30 | MeC(O)-C₆H₄-NH-C(O)-N(4-OH-2-C(O)NHtBu-piperidine) | 89%[f] | 161–163 |

TABLE 1-continued

Preparation of Ureas from Phenyl Carbamates and melting point.

| carbamates 1 | amine[a] | time[b] | ureas 2 | yield[c] | mp (° C.) |
|---|---|---|---|---|---|
| e | benzylamine (H₂N-CH₂-Ph) | 1 h | N-methyl-N'-benzyl urea | 84.5%[f] | 70–72 |
| f | NH₄OH[e] | 1 h | N-methylurea | 74.5%[f] | 135–137 |
| g | (S)-α-methylbenzylamine | 2 h 30 | corresponding urea | 92%[f] | 107–109 |
| h | 2-methyl-1-phenylpropan-2-amine | 15 min | corresponding urea | 95.5% | 105–107 |

(carbamates e, f, g: t-BuO₂C–CH(CH₂Ph)–NH–C(O)–OPh; carbamate h: MeO₂C–CH₂–C₆H₄–NH–C(O)–OPh)

TABLE 1-continued

Preparation of Ureas from Phenyl Carbamates and melting point.

| carbamates 1 | amine[a] | time[b] | ureas 2 | yield[c] | mp (° C.) |
|---|---|---|---|---|---|
| i | H2N-CH2-Ph | 1 h | benzyl-NH-C(O)-NH-Me | 80% | 85–87 |
| j | piperidine (HN) | 15 min | piperidine-C(O)-NH-Me | 78% | 126–128 |
| k | H2N-(4-piperidyl-NBn) | 3 h | (4-NBn-piperidyl)-NH-C(O)-NH-Me | 93% | 169–171 |
| l | HNBu2 | | no reaction | | |

[a] unless otherwise noted 1.05 eq. of amine was used
[b] DMSO at RT (conc. 0.5 M) and the time values
[c] yield of isolated pure product
[d] 1.05 eq of aq 10 N NaOH was used
[e] 1.1 eq of NH4OH was used
[f] optical rotations for ureas:
2a: $[\alpha]_D^{24}$ − 97.7° (C 2.12, MeOH);
2d: $[\alpha]_D^{24}$ − 153.6° (C 1.01, MeOH);
2e: $[\alpha]_D^{22}$ + 16.5° (C 1.1, MeOH);
2f: $[\alpha]_D^{22}$ + 20.4° (C 1.1, MeOH);
2g: $[\alpha]_D^{24}$ + 5.9° (C 0.66, MeOH).

For entry a, prolinol was used and the chiral urea 2a was isolated in 87% yield. No alcoholysis product was observed. The scope of the reaction was also extended to cover amines in aqueous solution such as NH$_4$OH (1.1 eq.) (entry f). No hydrolysis of the phenyl carbamate was observed. Reaction with secondary amines generated the N,N,N'-trisubstituted ureas in high yield within 15 minutes at ambient temperature (entries a,b,d and j). When the HCl-salt of the amine was used, it was neutralized in situ with an equimolar amount of 10N aqueous NaOH (entry b). Here again, no hydrolysis product was detected. Aromatic amines such as aniline (entry c) also reacted to form the appropriate urea, albeit this reaction required heating to 85° C. for one hour. In accordance with the finding of Lamothe et al., vide supra, the reaction time required was usually longer in the case of aliphatic carbamates versus aniline derived carbamates (60 instead of 15 minutes). The chiral and pharmaceutically important amine of entry d, see Gillard, J.; Abraham, A.; Anderson, P. C.; Beaulieu, P. L.; Bogri, T.; Bousquet, Y.; Grenier, L.; Guse, I., Lavallée, P.; *J. Org. Chem.,* 1996, 61, 2226, also gave an urea 2d at room temperature with an excellent yield. In contrast to the approach of Lamothe et al. vide supra, using strong base for carbamate deprotonation, compounds 2e, 2f and 2g were prepared under very mild condition and were determined to be enantiomerically pure (>99% ee). This method is not limited to the use of non-sterically hindered amines. In fact, hindered primary and secondary amines gave the products 2d and 2h in excellent yield (entries d, h). To explore further the utility of this method, the symmetrical urea 2k was prepared at ambient temperature in 93% yield, in contrast to the reaction conditions of several hours at 80° C. as reported by Freer et al., vide supra. Under our conditions, compound 2j was obtained in 90% yield in 15 minutes compared to 48 h using the magnesium salt of an amine as reported by Basha, vide supra.

Secondary amino carbamates do not react amines under the conditions of the present process. This aspect is illustrated in that all attempts to convert the carbamate of the secondary amine 11 into the corresponding urea failed even when heated at 190° C. for three hours.

Particularly interesting is the example involving the concomitant use of two amines with one carbamate. With reference to Scheme 1 hereinafter, the aminolysis was completed after 15 minutes and the ureas 2m and 2n were isolated in 93% overall yield with a ratio of 1:1. This result shows the method may have potential application in the field of combinatorial chemistry.

Scheme 1

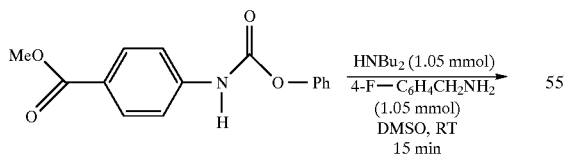

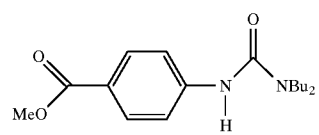

2m(47%)mp = 91–92 °C

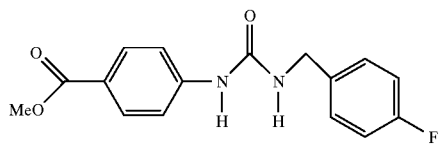

2n(46%)mp = 191–193 °C
(93% combined yield ratio, ratio 1:1)

It was found that the rate and the yield of the reaction were highly dependent on the solvent used, as exemplified in the preparation of urea 2o (Scheme 2, Table 2). Compared to dimethyl sulfoxide, the reaction was much slower in methanol, dioxane or ethylene glycol dimethyl ether, or in methylene dichloride in which the carbamate was insoluble at the beginning of the reaction. With tetrahydrofuran as solvent, a five hour reflux was required to complete the reaction. Dimethyl formamide could be used as a substitute for dimethyl sulfoxide, but slightly lower yields were observed (74 to 96%). Contrary to isocyanates in dimethyl formamide, Weiner, L. M.; J. Org. Chem., 1960, 25, 2245 or in dimethyl sulfoxide, Carleton, P. S.; Farrissey, W. J. Jr.; Tetrahedron Lett., 1969, 10, 3485, phenyl carbamates were very stable in dimethyl sulfoxide at ambient temperature. The high rate of the nucleophilic addition is obviously accelerated in dimethyl sulfoxide as illustrated in Table 2.

Scheme 2

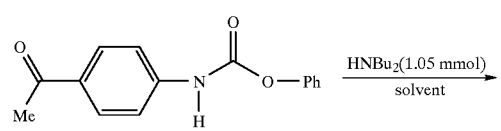

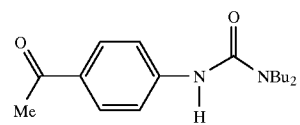

TABLE 2

Solvent Effect in Reaction of Carbamate 1d with Dibutylamine

| Solvent | DMSO | DMF | THF | MeCN | Dioxane | DME | $CH_2Cl_2$ | MeOH | Pyr |
|---|---|---|---|---|---|---|---|---|---|
| Condition | rt | rt | reflux | rt | reflux | rt | rt | rt | rt |
| Time[b] | 15 min | 15 min | 5 h | 1 h | 5 h | 24 h | 24 h | 24 h | 2.5 h |
| Yield[c] | 96% | 73.5% | 92.5% | 79% | 65% | 92% (3.5%) | 90% (9.5%) | 74% | 85.5% (2.5%) |

Note:
[a] 1.05 eq of amine was used
[b] the time values present an upper limit
[c] referred to pure isolated yield (yields in parentheses show recovered starting material)

Finally, the stability of a number of functional groups was examined under the present reaction conditions (Table 1) and the aminolysis product was isolated in high yields ranging from 74.5 to 95.5% without noticeable degradation. The generality of the method has been assessed using a variety of aromatic, aliphatic amines and amino acids which were reacted with phenyl carbamates derived from primary amine.

In conclusion, urea derivatives are formed in excellent yield under neutral and mild conditions when phenyl carbamates are treated with an amine in dimethyl sulfoxide at ambient temperature. The procedure described herein represents an improvement on existing methods for the synthesis of ureas. It avoids the use of phosgene or thiophosgene, the preparation of reagents and harsh conditions. The only by-product is phenol, which is easily removed by a 1N NaOH wash. For its simplicity and the mildness of the reaction condition, which do not require anhydrous media, this method should be useful for the preparation of a wide variety of ureas and thioureas.

EXAMPLES

The following examples further illustrate this invention. Temperatures are given in degrees Celsius. Solution percentages or ratios are expressed as a volume to volume relationship, unless stated otherwise. Nuclear magnetic resonance spectra were recorded on a Bruker 400 MHz spectrometer; the chemical shifts (δ) are reported in parts per million. Melting points are uncorrected. $^1$H (400 MHz) NMR and $^{13}$C NMR (100 MHz) spectra were recorded on a Bruker 400 MHz spectrometer using DMSO -d$_6$ solvent referenced at 2.50 and 39.51 ppm respectively. Elemental analyses (C,H,N) were carried out using a Fisons Instruments EA 1108 CHN elemental analyzer. MS and HRMS were recorded on a Micromass Autospec®. Specific optical rotations were measured in MeOH using the Na lamp (589 nm) of a Perkin Elmer 241 polarimeter. HPLC analyses were performed on a Vydac C-18 column using MeCN/H$_2$O with 0.06% TFA. All solvents used were anhydrous grade. Phenyl chloroformate and the various amines were purchased from Aldrich and used as is. All of the phenyl carbamates were analyzed for C H N and/or high resolution FAB mass spectroscopic and the results agreed to ±0.4% of the theoretical values. The yields reported in this work were of the purified product, unless stated otherwise. Abbreviations or symbols used in the examples include Boc: tert-butoxycarbonyl or 1,1-dimethylethoxycarbonyl; DMSO: dimethyl sulfoxide; EtOAc: ethyl acetate; Et$_2$O: diethyl ether; FAB/MS: fast atom bombardment mass spectrometry; PFU: plaque forming units; THF: tetrahydrofuran.

Example 1

N'-(4-Acetylphenyl)-N,N-dibutylurea (compound of formula 2 wherein: X=O, R$_1$=4-CH$_3$CO-Ph, R$_2$=Bu and R$_3$=Bu)

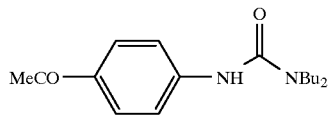

(a) Phenyl N-(4-Acetylphenyl)carbamate (1d)

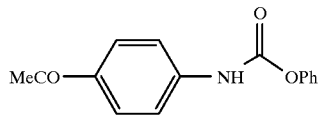

A dry 500 mL flask equipped with an N$_2$ inlet adapter, a rubber septum and a magnetic stirring bar, was charged with 4-aminoacetophenone (13.5 g, 100 mmol) in dry THF (200 mL). The mixture was cooled to 0°. To the mixture were added slowly pyridine (10.1 mL, 125 mmol) and phenyl chloroformate (12.9 mL, 103 mmol). The resulting suspension was stirred at 0° for 5 min and allowed to warm to room temperature (20–22°) for 1 h. EtOAc (600 mL) was added and the suspension was washed successively with aqueous 1N HCl (100 mL), H$_2$O (100 mL), saturated aquous NaHCO$_3$ (200 mL), brine (100 mL), dried (MgSO$_4$) and concentrated under reduced pressure to give the crude product. The latter was triturated with Et$_2$O/hexane (hot) to yield 23.9 g (94% yield) of 1d as an off white solid; mp: 167–169°

$^1$H NMR (DMSO-d$_6$) δ 10.62 (s, 1H), 7.94 (d, 2H, J=9.0), 7.65 (d, 2H, J=9.0), 7.46–7.43 (m, 2H), 7.30–7.24 (m, 3H), 2.53 (s, 3H).

$^{13}$C NMR (DMSO-d$_6$) δ 196.5, 151.6, 150.3, 143.2, 131.5, 129.6, 129.5, 125.6, 121.9, 117.6, 26.4.

MS FAB m/z=256 [MH]$^+$

HRMS: m/z Calcd for C$_{15}$H$_{14}$NO$_3$ 256.0973 ; Found 256.0965.

(b) N'-(4-Acetylphenyl)-N,N-dibutylurea (title compound)

In a dry 100 mL flask equipped with an N$_2$ inlet adapter, a rubber septum and a magnetic stirring bar, was placed phenyl N-(4-acetylphenyl)carbamate (6.38 g, 25 mmol) in DMSO (50 mL). Dibutylamine (4.42 mL, 26.25 mmol) was slowly added to the mixture. The resulting solution was stirred at room temperature for 15 min, after which time EtOAc (250 mL) was added to the reaction mixture. The latter was washed successively with H$_2$O (2×50 mL), aqueous 1N HCl (100 mL), H₂O (100 mL), aqueous 1N NaOH (100 mL) and brine (100 mL), dried (MgSO₄) and concentrated under reduced pressure to give a crude solid. The solid was triturated with Et₂O/hexane to yield 6.98 g (96% yield) of the title compound as a white solid.

mp : 90–92°

¹H NMR (DMSO-d₆) δ 8.50 (s,1H), 7.84 (d, 2H, J=8.7), 7.62 (d, 2H, J=8.7), 3.32–3.29 (m, 4H), 2.49 (s, 3H), 1.48–1.44 (m, 4H), 1.30–1.27 (m, 4H), 0.89 (t, 6H, J =7.5).

¹³C NMR (DMSO-d₆) δ 196.2, 154.3, 145.6, 130.1, 129.0, 118.3, 46.1, 30.2, 26.2, 19.5, 13.8.

MS FAB m/z=291 [MH]⁺C₁₇H₂₅N₂O₂ Calcd C 70.31 H 9.02 N 9.65 (290.41) Found 70.47 9.12 9.71

Example 2

N'-{4-(2-Amino-4-thiazolyl)phenyl}-N-methyl-N-{2-(2-pyridinyl)ethyl}urea (compound of formula 2 wherein: X=O, R₁=4-(2-amino-4-thiazolyl)phenyl, R₂=Me and R₃=2-(2-pyridinyl)ethyl

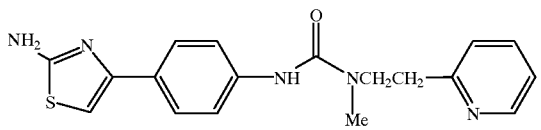

(a) 2,2,2-Trichloroethyl N-{4-(2-amino-4-thiazolyl) phenyl}carbamate:

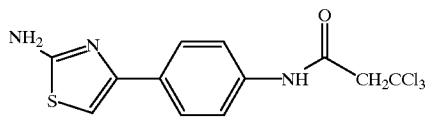

2,2,2-Trichloroethyl chloroformate (72.3 mL, 0.52 mol) was added (5 min) to an ice cold suspension of 4'-aminoacetophenone (67.6 g, 0.50 mol, Aldrich Chemical Co., Milwaukee, Wis., U.S.A.) and pyridine (50.5 mL, 0.62 mol) in CH₂Cl₂ (1 L). The reaction mixture was stirred at 0° for 15 min and then at room temperature (20–22°) for 45 min. The solvent was removed under reduced pressure. Et₂O (500 mL) and aqueous 1N HCl (500 mL) were added to the residue. The resulting solid was collected by filtration, washed with H₂O (1 L) and Et₂O (1 L) and dried over P₂O₅ in a desiccator under reduced pressure for 15 h to yield the expected carbamate (137.8 g, 89% yield). A mixture of the crude carbamate (137.8 g, 0.44 mol), thiourea (135.0 g, 1.77 mol) and I₂ (202.6 g, 0.80 mol) in isopropanol (670 mL) was heated at reflux for 18 h. The reaction mixture was cooled to room temperature and EtOAc (1 L) was added. The solution was washed serially with H₂O (2×600 mL), saturated aqueous NaHCO₃ (2×1 L) and H₂O (2×1 L). A mixture of the organic layer and 4N aqueous HCl (750 mL) was stirred vigorously at room temperature for 1.5 h. Et₂O (~800 mL) and H₂O (~300 mL) were added to the mixture to facilitate stirring. The suspension was filtered and the solid was washed with a 1:1 mixture of EtOAc and Et₂O (2 L). The solid was suspended in 20% aqueous NaOH (1.2 L) and the mixture was extracted with EtOAc (2 L). The EtOAc extract was washed with brine (700 mL), dried (MgSO₄), and concentrated under reduced pressure to yield 2,2,2-trichloroethyl N-{4-(2-amino-4-thiazolyl)phenyl}carbamate (117.7 g, 75% yield) as a pale yellow solid: ¹H NMR (DMSO-d₆) δ 10.18 (s,1H), 7.74 (d,J=8.6 Hz, 2H), 7.51 (d,J-8.6 Hz, 2H), 7.01 (s, 2H) 6.88 (s, 1H), 4.95 (s, 2H); MS (FAB) m/z 366/368/370/372 (MH)⁺.

(b) tert-Butyl N-{4-(4-Aminophenyl)-2-thiazolyl}carbamate

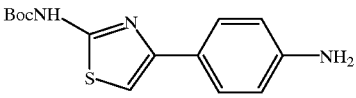

A solution of (Boc)₂O (87.7 g, 0.40 mol) in CH₂Cl₂ (85 mL) and 4-(dimethylamino)pyridine (4.08 g, 33.0 mmol) was added (10 min) to a cooled (0°) solution of the product of the preceding section (a) (117.7 g, 0.33 mol) and pyridine (135.0 mL, 1.67 mol) in THF (500 mL) and CH₂Cl₂ (1 L). The reaction mixture was stirred at room temperature for 15 h. The reaction mixture was diluted with EtOAc (1.5 L) and Et₂O (1 L). The resulting solution was washed serially with H₂O (1 L), 10% (w/v) aqueous citric acid (2×500 mL), aqueous 1N HCl (500 mL), H₂O, saturated aqueous NaHCO₃ (2×1 L) and brine (1 L), dried (MgSO₄) and concentrated under reduced pressure to give a pale yellow foam (163 g). The latter foam (160 g, 0.34 mol) was diluted in 1,4-dioxane (1.72 L) and the solution cooled to 10°. Zinc powder (224 g, 3.43 mol) and aqueous 1N HCl (3.4 L) were added to the cooled solution. The reaction mixture was mechanically stirred at room temperature for 1.5 h. The suspension was filtered and the collected material was washed with aqueous 1N HCl (~1 L). Aqueous 20% NaOH (2 L) was added to the filtrate (including the acidic wash). The resulting mixture was extracted with EtOAc (9 L total). The EtOAc extract was filtered through diatomaceous earth. The filtrate was washed with brine, dried (MgSO₄) and concentrated under reduced pressure. Purification by flash chromatography (SiO₂, EtOAc: hexane, 1:2 to 2:3) of the residue gave tert-butyl N-{4-(4-aminophenyl)-2-thiazolyl}carbamate (48.3 g, 43% yield) as a pale yellow foam: ¹H NMR (DMSO-d₆) δ 11.40 (s, 1H), 7.52 (d, J=7.2 Hz, 2H), 7.12 (s, 1H), 6.57 (d, J=7.2 Hz, 2H), 5.20 (s, 2H), 1.48 (s, 9H); MS (FAB) m/z 292 (MH)⁺.

c) Phenyl N-{4-{2-{{(1,1-dimethylethoxy) carbonyl}amino}-4-thiazolyl}phenyl}carbamate

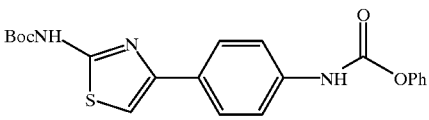

The product of the preceding section (b) (3.50 g, 12.01 mmol) was dissolved in THF (36 mL) and cooled to 0°. Triethylamine (3.34 mL, 24.02 mmol) was added to the cold solution followed by the dropwise addition of phenyl chloroformate (1.58 mL, 12.61 mmol). The reaction mixture was stirred at 0° for 15 min and then at room temperature (20–22°) for 1.5 h. Thereafter, EtOAc (500 mL) was added and the resultant mixture was washed serially with aqueous 1N HCl (2×50 mL), H₂O (2×50 mL), saturated aqueous NaHCO₃ solution and brine, dried (MgSO₄) and concentrated to dryness. The residue was triturated with warm Et₂O/hexane (1:30). The resulting solid was collected and dried under reduced pressure to give the desired carbamate (4.70 g, 95% yield) as a light ivory solid: ¹H NMR(DMSO-d₆) δ 11.54 (s, 1H), 10.30 (s, 1H), 7.82 (d,J=8.7 Hz, 2H), 7.56 (d,J=8.7 Hz, 2H), 7.43 (m, 2H), 7.24 (m,3H), 1.49 (s, 9H).

d) The title compound

A solution of the product of the preceding section (c) (2.67 g, 6.5 mmol) and N-methyl-N-{2-(2-pyridinyl)

ethyl}amine (0.94 mL, 6.82 mmol) in DMSO (14 mL) was stirred at room temperature for 2 h. The reaction mixture was diluted with EtOAc (150 mL), washed with H$_2$O (2×50 mL), 5% (w/v) aqueous citric acid (30 mL), saturated aqueous NaHCO$_3$ solution and brine, dried (MgSO$_4$),treated with charcoal, filtered through diatomaceous earth and concentrated. The residue was purified by flash chromatography (SiO$_2$, EtOAc followed by isopropanol: CH$_2$Cl$_2$, 1:15) to give the Boc derivative of the title compound (1.81 g, 65 yield) i.e.

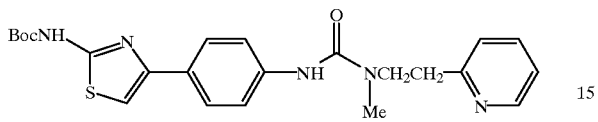

$^1$H NMR (DMSO-d$_6$) δ 11.50 (s,1H),8.51 (broad s,1H), 8.44 (s,1H), 7.71 (d,J=8.90 Hz,2H), 7.70 (s,1H), 7.49 (d,J= 8.9 Hz,2H), 7.37(s,1H), 7.32 (broad d,J=7.6 Hz,1H), 7.22 (broad t, J=6.0 Hz, 1H), 3.69(t,J=6.4 Hz,2H), 2.99(t,J=6.4 Hz,2H), 2.90 (s,3H), 1.49 (s,9H); MS(FAB) m/z 454 (MH)$^+$.

The latter Boc derivative was reacted with an excess of trifluoroacetic acid in CH$_2$Cl$_2$ solution at room temperature for 3h. The solution was concentrated under reduced pressure to give the title compound in a quantitive yield:

$^1$H NMR (DMSO-d$_6$) δ 8.52 (d, J=4.5 Hz, 1H), 8.39 (s, 1H), 7.71 (~ddd, J=7.8, 7.5, 1.8 HZ, 1H), 7.65 (d, J=8.7 HZ, 2H), 7.44 (d, J=8.7 Hz, 2H), 7.31 (d, J=7.8 Hz, 1H), 7.22 (broad dd, J=7.5, 4.5 Hz, 1H), 6.96 (s, 2H), 6.82 (s, 1H), 3.70 (t, J=7.2 Hz, 2H), 3.00 (t, J=7.2 Hz, 2H), 2.90 (s, 3H); MS (FAB) m/z 354 (MH)$^+$.

Example 3

N'-{4-(2-Amino-4-thiazolyl)phenyl}-N,N-dibutyl}urea (compound of formula 2 wherein: X= O, R$_1$=4-(2-amino-4-thiazolyl)phenyl, R$_2$=Bu and R$_3$=Bu)

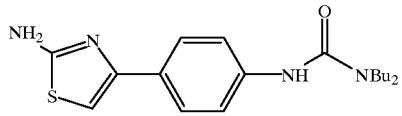

(a) Phenyl N-{4-(2-amino-4-thiazolyl)phenyl}carbamate

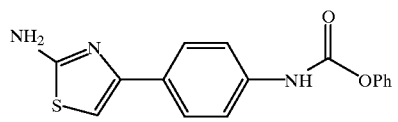

The product of example 1(c) was reacted with an excess of trifloroacetic acid in CH$_2$Cl$_2$ solution at room temperature for 3h. Concentration of the reaction mixture under reduced pressure gave the desired phenyl carbamate:

$^1$H NMR (DMSO) δ 10.30 (S, 1H), 7.71 (d, J=8.4 Hz, 2H), 7.50 (d, J=8.4 Hz, 2H), 7.45–7.41 (m, 2H), 7.28–7.22 (m, 3H), 7.05 (s, 2H), 6.88 (S, 1H).

(b) The title compound

A solution of the product of the preceding section (a) (4.67 g, 15.0 mmol) and N,N-dibutylamine (2.65 mL, 15.8 mmol) in DMSO (30 mL) was stirred at room temperature for 2.5 h. The reaction mixture was diluted with EtOAc (150 mL), washed serially with H$_2$O (2×50 mL), 10% (w/v) aqueous NaHCO$_3$ solution (2×50 mL), and brine, dried (MgSO$_4$) and concentrated to dryness. The solid residue was triturated with Et$_2$O/hexane (5:1). The resultant mixture was stirred with ultrasound. The solid was collected by filtration and rinsed with Et$_2$O to give the title compound (4.08 g, 79% yield) as a yellowish solid.

$^1$H NMR (DMSO-d$_6$) δ 8.14 (s, 1H), 7.64 (d, J=8.7 Hz, 2H), 7.45 (d, J=8.7 Hz, 2H), 6.96 (s, 2H), 6.81 (s, 1H); 3.28 (t, 7.2 Hz, 4H), 1.52–1.42 (m, 4H), 1.34–1.21 (m, 4H), 0.90 (t, J=7.2 Hz, 6H); MS (FAB) m/z 347 (MH)$^+$.

Example 4

N'-{4-(2-Amino-4-thiazolyl)phenyl}-N-methyl-N-{2-(2-pyridinyl)ethyl}thiourea (compound of formula 2 wherein: X=S, R$_1$=4-(2-amino-4-thiazolyl)phenyl, R$_2$=Me and R$_3$=2-(2-pyridinyl) ethyl

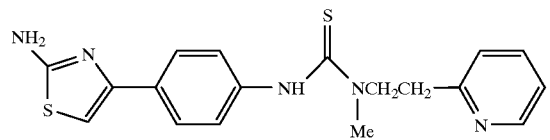

(a) Phenyl N-{{4-{2-{{(1,1-dimethylethoxy)carbonyl}-amino}-4-thiazolyl}phenyl}thiocarbamate

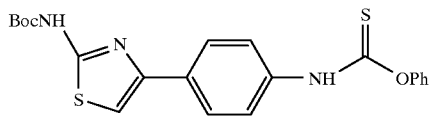

The product of section (b) of example 2 (1.75 g, 6.00 mmol) was dissolved in THF (24 mL) and cooled to 0°. Triethylamine (1.67 mL, 12.01 mmol) was added to the cold solution followed by the dropwise addition of phenylchlorothionoformate (0.87 mL, 6.30 mmol). The reaction mixture was stirred at 0° for 2 h. Thereafter, EtOAc (150 mL) was added and the resultant mixture was washed serially with aqueous 1N HCl (2×30 mL), H$_2$O (2×50 mL), saturated aqueous NaHCO$_3$ solution and brine, dried (MgSO$_4$) and concentrated to dryness. The residue was used to the following section (b) without any further purification.

(b) The title compound

A solution of the product of the preceding section (a) (0.35 g, 0.81 mmol) and N-methyl-N-{2-(2-pyridinyl) ethyl}amine (0.12 mL, 0.85 mmol) in DMSO (2 mL) was stirred at room temperature for 2 min. The reaction mixture was diluted with EtOAc (100 mL), washed with H$_2$O (2×30 mL), brine, dried (MgSO$_4$) and concentrated. The residue was purified by flash chromatography (SiO$_2$, 1:2 (EtOAc:hexane) followed by EtOAc to give the title compound (250 mg, 65% yield): $^1$H NMR (DMSO-d$_6$) δ 11.55 (s, 1H), 9.22 (broad s, 1H), 8.52 (broad s, 1H), 7.79–7.73 (m, 3H), 7.78 (d, J=8.7 Hz, 2H), 7.75–7.72 (m, 1H), 7.98 (s, 1H), 7.36 (d, J=8.7 Hz, 2H), 7.36–7.33 (m, 1H), 7.25 (broad t, J=6 Hz, 1H), 4.16 (t, J=6.6 Hz, 1H), 3.2 (s, 3H), 3.12 (t, J=6.6 Hz, 1H), 1.50 (s, 9H); MS(FAB) m/z 470 (MH)$^+$.

Example 5

N'-{4-{2-{{(1,1-Dimethylethoxy)carbonyl}amino}-4-thiazolyl}phenyl}-N,N-dibutyl}thiourea (compound of formula 2 wherein: X=S, $R_1$=4-{2-{{(1,1-dimethylethoxy)carbonyl}amino}-4-thiazolyl}phenyl, $R_2$=Bu and $R_3$=Bu)

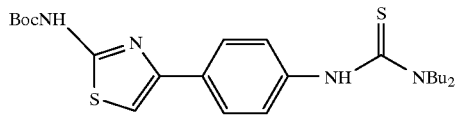

A solution of the product of section (a) of example 4 (0.91 g, 2.12 mmol) and N,N-dibutylamine (0.38 mL, 2.23 mmol) was stirred at room temperature for 1 min. The reaction mixture was diluted with EtoAc (100 mL), washed with $H_2O$ (2×50 mL), aqueous 1N HCl (50 mL), saturated aqueous $NaHCO_3$ solution (2×30 mL) and brine, dried ($MgSO_4$) and concentrated. The residue was purified by flash chromatography ($SiO_2$, 1:3 (EtOAc:hexane)) to give the title thiourea compound (615 mg, 62%) as a white solid.

$^1$H NMR (DMSO-$d_6$) δ 11.50 (s, 1H), 8.93 (s, 1H), 7.79 (d, J=8.4 Hz, 2H), 7.49 (s, 1H), 7.33 (d, J=8.4 Hz, 2H), 3.72 (broad s, 4H), 1.65–1.55 (m, 4H), 1.50 (s, 9H); 1.35–1.25 (m, 4H), 0.92 (t, J=7.2 Hz, 6H); MS (FAB) m/z 463 (MH)$^+$.

TABLE 3

Spectroscopic Data of Ureas 2 noted in Table 1

| Compound | $1_H$ NMR (DMSO-$d_6$) δ(ppm), J(Hz) | $^{13}$C NMR (DMSO $d_{-6}$) δ(ppm) | FAB-MS m/z (%) | CHN (%) |
|---|---|---|---|---|
| 2a | 8.96(bs, 1H), 7.85(d, 2H, J=8.7), 7.60 (d, 2H, J=8.7), 5.34(bs, 1H), 3.96(bs, 1H), 3.80(s, 3H), 3.47–3.39(m, 4H), 1.93–1.77(m, 4H) | 166.0, 154.1, 145.3, 130.0, 122.0, 117.9, 63.5, 58.9, 51.6, 46.6, 27.7, 23.2 | 279(100; MH$^+$), | $C_{14}H_{18}N_2O_4$(278.31) Calcd   C 60.42  H 6.52  N 10.07 Found       60.34     6.57    9.96 |
| 2b | 8.65(s, 1H), 7.84(d, 2H, J=8.6), 7.63 (d, 2H, J=8.6), 3.80(s, 3H), 2.94(s, 6H) | 166.8, 156.0, 146.4, 130.7, 122.9, 119.2, 52.5, 37.1 | 223(100, MH$^+$), | $C_{11}H_{14}N_2O_3$(222.25) Calcd   C 59.45  H 6.35  N 12.60 Found       59.48     6.34   12.55 |
| 2c | 9.17(s, 1H), 8.83(s, 1H), 7.74(d, 2H, J=8.7), 7.64(d, 2H, J=8.9), 7.46(d, 2H, J=8.9), 7.30(t, 2H, J=7.5), 7.00 (t, 1H, J=7.5) | 152.9, 145.0, 140.0, 134.1, 129.7, 123.2, 120.1, 119.4, 118.8, 104.1 | 238(100, MH$^+$), | $C_{14}H_{12}N_3O$(237.26) Calcd   C 70.87  H 4.62  N 17.71 Found       70.49     4.71   17.66 |
| 2d | 8.98(s, 1H), 7.87(d, 2H, J=8.9), 7.61 (d, 2H, J=8.9), 7.31(s, 1H), 4.83(d, 1H, J=4.4), 4.53(quint., 1H, J=6.4), 3.86(m, 1H), 3.74(m, 1H), 3.51(dt, 1H, J=13.0, 3.4), 2.50(s, 3H), 2.05–1.98 (m, 1H), 1.86–1.80(m, 1H), 1.71–1.53 (m, 2H), 1.25(s, 9H) | 197.1, 172.2, 156.3, 146.2, 131.1, 130.0, 119.0, 62.9, 53.8, 51.0, 38.5, 34.4, 33.0, 29.3, 27.1 | 362(35, MH$^+$), 201(50) | $C_{19}H_{27}N_3O_4$(361.44) Calcd   C 63.14  H 7.53  N 11.63 Found       63.02     7.59   11.48 |
| 2e | 7.30–7.18(m, 10H), 6.54(t, 1H, J=6.0), 6.19(d, 1H, J=8.3), 4.35(q, 1H, J=7.2), 4.19(d, 2H, J=6.0), 2.91(m, 2H), 1.33(s, 9H) | 171.6, 157.4, 140.6, 137.2, 129.3, 128.2, 128.1, 126.9, 126.5, 126.4, 80.5, 54.5, 42.8, 38.0, 27.6 | 355(10, MH$^+$), 299(60) | $C_{21}H_{26}N_2O_3$(354.45) Calcd   C 71.16  H 7.39  N 7.90 Found       70.88     7.54    7.88 |
| 2f | 7.31–7.14(m, 5H), 6.18(d, 1H, J=8.4), 5.60(s, 2H), 4.29(q, 1H, J=8), 2.90 (dd, 1H, JAB=11.7, JAX=6.6), 2.86 (dd, 1H, JAB=11.7, JBX=7.9), 1.30 (s, 9H) | 171.7, 157.9, 137.2, 129.3, 128.1, 126.4, 80.4, 54.2, 38.0, 27.6 | 265(20, MH$^+$), 209(100) | $C_{14}H_{20}N_2O_3$(264.33) Calcd   C 63.62  H 7.63  N 10.60 Found       63.69     7.69   10.60 |
| 2g | 7.32–7.13(m, 10H), 6.59(d, 1H, J=8.3), 6.03(d, 1H, J=8.3), 4.70(quint, 1H, J=7.0), 4.29(q, 1H, J=6.6), 2.90 (dd, 1H, JAB=11.6, JAX=6.6), 2.86 (dd, 1H, JAB=11.6, JBX=7.0), 1.33 (s, 9H), 1.30(d, 3H, J=7.0) | 169.9, 155.0, 144.0, 135.5, 127.8, 126.6, 126.5, 124.9, 124.1, 79.0, 52.7, 47.0, 36.4, 26.0, 21.7 | 369(10, MH$^+$), 313(25), 180(75), 120(100) | $C_{22}H_{28}N_2O_3$(368.48) Calcd   C 71.71  H 7.66  N 7.60 Found       71.95     7.76    7.67 |
| 2h | 8.22(s, 1H), 7.33–7.12(m, 9H), 5.73(s, 1H), 3.60(s, 3H), 3.57(s, 2H), 3.00(s, 2H), 1.22(s, 6H) | 172.7, 155.3, 140.2, 139.3, 131.1, 130.4, 128.6, 127.4, 126.7, 118.3, 53.1, 52.4, 45.1, 28.3 | 341(100, MH$^+$) | $C_{20}H_{24}N_2O_3$(340.43) Calcd   C 70.57  H 7.11  N 8.23 Found       70.22     7.12    8.15 |
| 2i | 7.32–7.19(m, 5H), 6.41(t, 1H, J=6), 6.00(t, 1H, J=6.6), 4.19(d, 2H, J=6), 4.06(q, 2H, J=7.2), 3.25(q, 2H, J=6.3), 2.42(t, 2H, J=6.6), 1.18(t, 3H, J=7.2) | 171.7, 157.9, 140.8, 128.1, 127.0, 126.5, 59.8, 42.9, 35.4, 34.9, 14.1 | 251(100, MH$^+$) | $C_{13}H_{18}N_2O_8$(250.30) Calcd   C 62.38  H 7.25  N 11.19 Found       62.57     7.24   11.20 |
| 2j | 8.22(s, 1H), 7.32(d, 2H, J=8.9), 6.80 (d, 2H, J=8.9), 3.69(s, 3H), 3.39–3.35 (m, 4H), 1.56–1.52(m, 2H), 1.49–1.45 (m, 4H) | 156.0, 155.1, 134.6, 122.3, 114.3, 55.9, 45.4, 26.3, 25.0 | 235(100, MH$^+$) | $C_{13}H_{18}N_2O_2$(234.30) Calcd   C 66.64  H 7.74  N 11.96 Found       66.65     7.84   11.87 |
| 2k | 7.32–7.21(m, 10H), 5.66(d, 2H, J=8.0), 3.42(s, 4H), 3.38–3.30(m, 2H), 2.67(bd 4H, J=10.8), 2.00(t, 4H, J=10.8), 1.71(bd, 4H, J=10), 1.28(q, 4H, J=10.5) | 157.4, 139.3, 129.4, 128.8, 127.5, 62.9, 52.6, 46.8, 33.2 | 407(100, MH$^+$) | $C_{25}H_{34}N_4O$(406.58) Calcd   C 73.86  H 8.43  N 13.78 Found       73.69     8.57   13.75 |
| 2m | 8.49(s, 1H), 7.83(d, 2H, J=8.9), 7.63 (d, 2H, J=8.9), 3.80(s, 3H), 3.32(s, 4H), 1.52–1.44(m, 4H), 1.32–1.23(m, | 168.5, 156.8, 148.0, 132.3, 124.4, 121.0, 54.1, 48.5, 32.7, 21.9, 16.2 | 307(100, MH$^+$) | $C_{17}H_{26}N_2O_3$(306.41) Calcd   C 66.64  H 8.55  N 9.14 Found       66.59     8.62    9.14 |

TABLE 3-continued

Spectroscopic Data of Ureas 2 noted in Table 1

| Compound | $1_H$ NMR (DMSO-$d_6$) δ(ppm), J(Hz) | $^{13}$C NMR (DMSO $d_{-6}$) δ(ppm) | FAB-MS m/z (%) | CHN (%) |
|---|---|---|---|---|
| 2n | 4H), 0.89(t, 6H, J=7.3) 8.90(s, 1H), 7.84(d, 2H, J=8.7), 7.54 (d, 2H, J=8.7), 7.36–7.32(m, 2H), 7.17–7.13(m, 2H), 6.78(bs, 1H), 4.28 (d, 2H, J=5.7), 3.31(s, 3H) | 166.0, 163.2, 160.0, 155.6, 145.9, 137.1, 131.2, 130.0, 129.9, 122.6, 117.7, 115.9, 115.7, 52.5, 42.9 | 303(100, MH$^+$) | $C_{16}H_{15}N_2O_3F$(302.31) Calcd  C 63.57  H 5.00  N 9.27 Found     63.23    4.98    9.17 |

Example 7

The antiviral activity of the title compounds of Examples 2 and 3 can be demonstrated in biochemical, microbiological and biological procedures. For example, the activity of the compounds against herpes simplex type 1 (HSV-1) replication can be demonstrated in the following cell culture assay:

Assay

BHK-21 cells clone 13 (ATCC CCL10) were incubated for two days in 850 cm$^2$ roller bottles (2×10$^7$ cells/bottle) with α-MEM medium (Gibco Canada Inc., Burlington, Ontario, Canada) supplemented with 8% (v/v) fetal bovine serum (FBS, Gibco Canada, Inc.). The cells were trypsinized and then 3,000 cells in 100 μL of fresh medium were transferred into each well of a 96-well microtiter plate. The cells were incubated at 37° for a period of 3 days to reach a density of 50,000 cells per well. The cells were washed twice with 100 μL of α-MEM supplemented with 2% heat inactivated FBS and incubated for 1–2 h in 100 μL of the same medium.

Thereafter, the cells were infected with HSV-1 strain F or KOS (multiplicity of infection=0.05 PFU/cell) in 50 μL of α-MEM supplemented with 2% heat inactivated FBS. Following 1 h of virus absorption at 37°, the medium was removed and the cells were washed with α-MEM supplemented with 2% heat inactivated FBS (2×100 μL). The cells were incubated with or without 100 μL of the appropriate concentration of test reagent in α-MEM medium supplemented with 2% heat inactivated FBS. After 24 h of incubation at 37°, the extent of viral replication was determined by an ELISA assay; for instance, the following assay that detects the late glycoprotein C of HSV-1.

Cells were fixed in the microtiter plate with 100 μL of 0.063% glutaraldehyde in phosphate buffered saline for 30 min at room temperature. The microtiter plate was then washed once with casein blocking solution and blocked with 200 μL of the same solution for 1 h at room temperature. Thereafter, 100 μL of mAb C11 recognizing the glycoprotein C of HSV-1 (see E. Trybala et al., Journal of General Virology, 1994, 75, 743) was added to each well for 2 h at room temperature. The plate was washed three times with phosphate buffered saline containing 0.05% polyoxyethylene (20) sorbitan monooleate. The cells were incubated with 100 μL of sheep anti-mouse IgG horseradish peroxidase for 1 h at room temperature in the dark.

The plate was washed three times with 200 μL of the above-noted phosphate buffer saline preparation, and then once with 0.1M sodium citrate (pH 4.5). Thereafter, 100 μL of orthophenylenediamine dihydrochloride (OPD, Gibco, Canada Inc.) was added to each well. The plate was agitated on a microplate shaker for 30 min in the dark. Color development was monitored at 450 nm using a microplate spectrophotometer.

SAS was used to calculate % inhibition of viral replication and to generate $EC_{50}$ values.

In the preceding assay, the title compound of example 1 gave an $EC_{50}$=1.4 μM and the title compound of example 2 gave $EC_{50}$=0.8 μM.

When an urea derivative such as the title compound of examples 2 and 3 is employed as an antiviral agent, it is administered orally, topically or systemically to humans in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier. For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the urea derivative is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Pratice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the urea derivative will vary with the form of administration and the particular active agent chosen. Furthermore, it will vary with the particular host under treatment. Generally, treatment is initiated with small increments until the optimum effect under the circumstance is reached. In general, the inhibitor compound is most desirably administered at a concentration level that will generally afford antivirally effective results without causing any harmful or deleterious side effects.

For oral administration, the urea derivative is administered in the range of 10 to 200 mg per kilogram of body weight per day, with a preferred range of 25 to 150 mg per kilogram.

With reference to topical application, the urea derivative is administered topically in a suitable formulation to the infected area of the body e.g. the skin, the eye, the genitalia or part of the oral cavity, in an amount sufficient to cover the infected area. The treatment should be repeated, for example, every 4 to 6 h until lesions heal.

For ocular administration, the urea derivative is administered either topically or intraocularly (injection or implant) in a suitable preparation. For example, an implant containing the compound in a suitable formulation can be surgically placed in the posterior segment of the eye through a small incision.

With reference to systemic administration, the urea derivative is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

I claim:

1. A process for preparing a urea derivative which comprises reacting a primary phenyl carbamate or phenyl thiocarbamate with ammonia, a primary amine, or secondary amine, in dimethyl sulfoxide solution to give the corresponding urea derivative.

2. The process as claimed in claim 1 which comprises reacting the carbamate derivative of the formula 1:

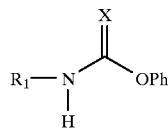

(1)

wherein X is oxo or thioxo and $R_1$ is lower alkyl, a monosubstituted or disubstituted lower alkyl wherein the substituent is selected from the group consisting of lower alkoxycarbonyl and phenyl; 4-{1-(phenylmethyl) piperidinyl}, phenyl or phenyl monosubstituted with a substituent selected from the group consisting of lower alkoxy, lower alkoxycarbonyl, cyano, lower alkanoyl and (lower alkoxycarbonyl)-(lower alkyl); 4-(2-amino-4-thiazoyl) phenyl or 4-{2-{{(1,1-dimethylethoxy)carbonyl}amino}-4-thiazolyl}phenyl with an amine of the formula Q:

$HNR_2R_3$ (Q)

wherein $R_2$ is hydrogen or lower alkyl and $R_3$ is hydrogen, lower alkyl, lower alkyl monosubstituted with phenyl or 2-pyridinyl; phenyl or 4-{1-(phenylmethyl)piperidinyl}; or $R_2$ and $R_3$ together with the nitrogen to which they are attached form a ring selected from the group consisting of

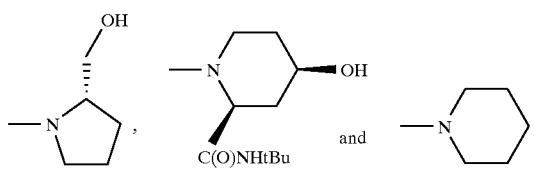

-continued

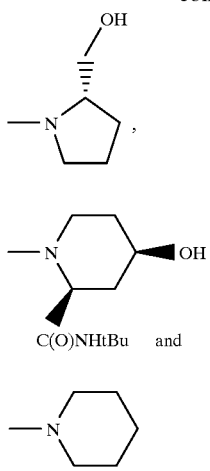

to obtain the corresponding urea derivative of formula 2:

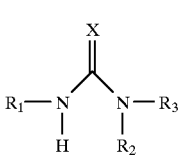

(2)

wherein X, $R_1$, $R_2$ and $R_3$ are as defined in this claim.

3. The process as claimed in claim 1 wherein the molar ratio of the phenyl carbamate or phenyl thiocarbamate to ammonia or to the primary or secondary amine ranges from 1:1 to 1:1.1.

4. The process as claimed in claim 1 wherein the reaction time ranges from instantaneously to three hours and the reaction temperature ranges from 22 to 100° C.

5. The process of claim 1 wherein the urea derivative is N'-{4-{(2-{{(1,1-dimethylethoxy)carbonyl}amino}-4-thiazolyl}phenyl}-N-{2-(2-pyridinylethyl}urea, the primary phenylcarbamate is phenyl N-{4-{2-{{(1,1-dimethylethoxy)carbonyl}amino}-4-thiazolyl}phenyl}carbamate and the amine is N-methyl-N-{2-(2-pyridinyl)ethyl}amine.

6. The process of claim 1 wherein the urea derivative is N'-{4-(2-amino-4-thiazolyl)phenyl}-N,N-dibutylurea, the primary phenylcarbamate is phenyl N-{4-(2-amino)-4-thiazolyl)phenyl}carbamate and the secondary amine is N,N-dibutylamine.

* * * * *